United States Patent [19]

Matsutani

[11] Patent Number: 4,501,312

[45] Date of Patent: Feb. 26, 1985

[54] METHOD FOR FORMING A HOLE OF EYELESS SUTURE NEEDLE

[75] Inventor: Kanji Matsutani, Takanezawa, Japan

[73] Assignee: Matsutani Seisakusho, Takanezawa, Japan

[21] Appl. No.: 304,196

[22] Filed: Sep. 21, 1981

[30] Foreign Application Priority Data

Jun. 29, 1981 [JP] Japan ................................. 56-99604

[51] Int. Cl.³ .............................................. B21G 3/18
[52] U.S. Cl. ...................................................... 163/5
[58] Field of Search .......... 10/26, 27 H, 27 E, 27 PH; 72/316, 318, 342, 358; 163/5, 4, 1

[56] References Cited

U.S. PATENT DOCUMENTS

| 2,620,028 | 12/1952 | Kohut | 163/5 |
| 2,621,344 | 12/1952 | Friedman | 10/26 X |
| 3,875,946 | 4/1975 | Duncan | 163/5 X |
| 4,159,686 | 7/1979 | Heim | 163/5 X |

FOREIGN PATENT DOCUMENTS 34690  11/1970  Japan ................................. 10/27 H

*Primary Examiner*—Mark Rosenbaum
*Attorney, Agent, or Firm*—Fleit, Jacobson, Cohn & Price

[57] ABSTRACT

A method for forming a suture-receiving hole in an eyeless suture needle. An oxidation resistant needle material and a heat resistant pressing tool are provided. The base end of the needle is heated to a temperature near its melting point and the heat resistant perforating tool is pressed into the base of the needle to form the desired suture-receiving hole. As an alternative, a preliminary hole can be formed in the base end of the needle material before the perforating tool is pressed into the hole as the final finishing step. Other variations include rotating or vibrating the perforating tool as it is pressed into the base end of the needle.

10 Claims, 13 Drawing Figures

(a)

(b)

METHOD FOR FORMING A HOLE OF EYELESS SUTURE NEEDLE

BACKGROUND OF THE INVENTION

1. Field of the Invention

This invention relates to a method for forming a suture-receiving hole in an eyeless suture needle characterized in that a hole is formed in the base end of a needle made from an oxidation resisting material, and more particularly to a method for forming a suture-receiving hole in an eyeless suture needle characterized in that a hole is formed by pressing a heat resisting perforating tool in the base end, after the base end of the needle material made of an oxidation resisting material was heated to near melting point.

2. Description of the Prior Art

The usual methods for forming a suture-receiving hole in an eyeless suture needle include: (1) a cutting processing method for cutting by a drill, (2) a weld processing method for welding a tubular member, (3) a discharge processing method for processing by discharging between electrodes in a liquid, and (4) special processing methods for causing the sublimation of a material by using an instantaneous high energy laser or electronic beam. However, all of the above methods have various problems as illustrated below. Also, they have a disadvantage in that it is difficult to cheaply form a hole having good character combining threads with high precision at the basic end of suture needle.

(1) The method for cutting a hole by use of a drill is difficult in the case of needle materials of stainless steel, especially when the hole is below 0.3 mm diameter, and cutting a deep hole of about 4-5 times the hole diameter becomes very costly in relation to the price of the needle and the life of the drill and is impractical.

(2) In the method of welding of a tubular member, welding of a tube to a thin solid material is very difficult, especially as the thickness of the tube becomes thin. There is also a possibility of failure the welding during the cutting process for the purpose of removal of weld flash and also the determination of hole-depth is complex and costly.

(3) In the discharge processing method, the processing speed is slow, and provides a hole that becomes a larger tapered shape at the bottom than at the inlet, and in a hole below 0.4 mm diameter the processing liquid does not circulate and the processing is nearly impossible. Naturally, attempts to make the electrode into a tube have been performed, but unless the hole diameter is fully expanded so that the processing liquid passes through a hole in the tube on account of the blind hole, the hole remains without receiving the processing and also this processing is unusable.

In the processing method (4) using a laser, an electronic beam and the like, wherein the material is heated instantaneously to a high temperature by laser light or an electronic beam, there is a fatal defect in that the shape of the hole is unstable and the accuracy is poor, because of sublimation of the material.

SUMMARY OF THE INVENTION

The method in accordance with the present invention is a quite new technique developed in consideration of these usual defects. Specifically, because in the present method the base end of the suture needle is heated to a given temperature, the method is concerned in a middle processing method such as three processing methods, that is, casting processing, hot forging processing and welding processing are used respectively at the same time.

Namely, this method is a processing method for forming a hole by making a perforating tool enter the base end of a needle, by pressing mutually, as if butt welding. The base end of the needle material is heated locally and instantaneously to or near the melting point, while held against a round rod or the like (a perforating tool) having a diameter corresponding to a desired hole size, and having a high melting point in comparison with the needle material (but the perforating tool has a good life at low temperature as much as possible). Accordingly, the processing temperature is higher than the hot forging temperature, and also is lower than the casting temperature which is carried out at a high temperature above the melting point, and becomes the temperature of butt welding or a little lower temperature than that temperature. Also, the processing power is not as large a power as in hot forging, but is not a power such as processing power "O" flowing in by dead load as in the case of casting. The processing power becomes nearly equal to or somewhat larger than the power used in butt welding, however the processing purpose is not to form a melting junction, and is closer to casting and hot forging and forming of materials without entirely deforming fusion of the tool.

DETAILED DESCRIPTION OF THE DRAWINGS

Figure 1:
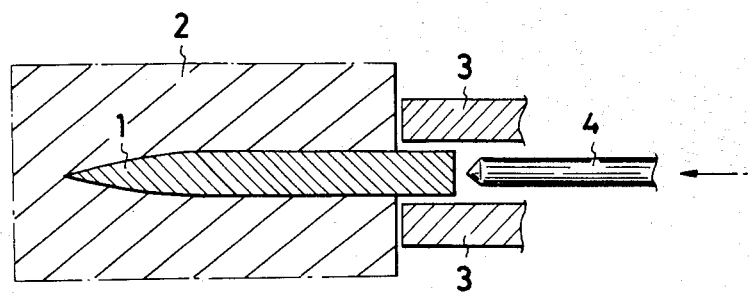
FIG. 1–FIG. 4 are cross-sectional views in which the steps of the method of the present invention are shown in order.
Figure 2:
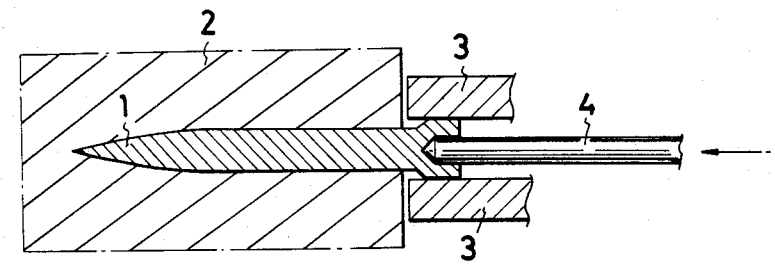
Figure 3:
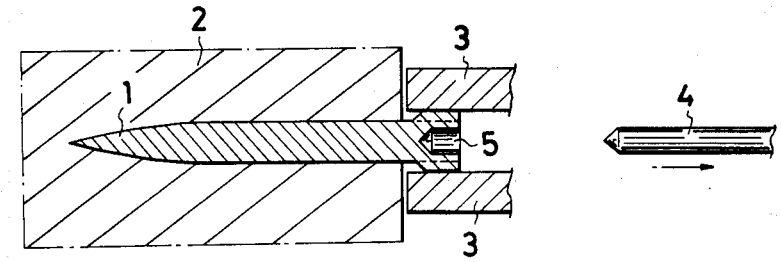
Figure 4:
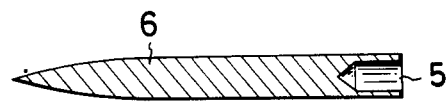
Figure 5:
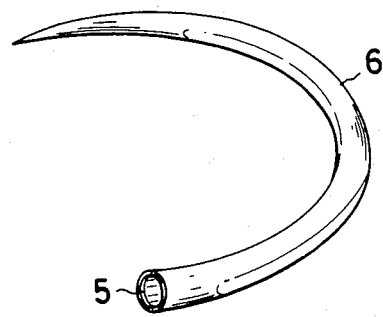
FIG. 5 is a perspective view of the finished suture needle.

Referring now to a specific embodiment in accordance with this invention as shown by the drawings, in FIG. 1–FIG. 5, 1 is a needle made of stainless steel, 2 is a holder of needle 1, 3 is an outer circumferential restraining tool of tubular shape capable of preventing the base end of needle 1 from deforming, 4 is a heat resisting performating tool. In performing the method of the present invention, the base end of needle 1 is first heated to near the melting point, thereafter a perforating tool 4 is forcibly pressed in the base end of needle 1 at the time of this state, perforating tool 4 is extracted and a hole 5 is formed in the base end of said needle material 1. A projecting portion formed on the outer circumferential surface of the base end on account of the formation of this hole 5 is cut off. An eyeless suture needle 6 having a hole 5 in the base end can be manufactured by curvedly processing the needle 1 to a prescribed shape.

In carrying out the method of the present invention, various oxidation resisting materials can be used for the needle material 1 and in the case of steel, the following stainless steels are especially effective.

13 Cr Stainless Steel (13% Cr) (Martensite system)
   Standard SUS 410,420 ... melting point 1430°–1530° C.
18–8 Stainless Steel (18% Cr, 8% Ni) (Austenite system)
   Standard SUS 304, 302 ... melting point 1400°–1450° C.
Precipitation hardening stainless steel
   Standard SUS 630-17-4 PH stainless (17% Cr, 4% Ni, 4% Cu)
   Standard SUS 631-17-7 PH stainless (17% Cr, 7% Ni, 1% Al)
   Melting point ... 1400°–1500° C.

With regard to the material used for perforating tool 4 in the aforesaid example, substances having a high melting point such as the following are considered.

|  | Symbol | Melting Point C | Electrical Resistance | Young's Modulus kg/cm |
|---|---|---|---|---|
| Tungsten | W | 3,410 ± 20 | 5.5 | 35 |
| Molybdenum | Mo | 2,625 ± 50 | 5.17 | 42 |
| Carbon | C | 3,700 ± 100 | 1375 | 0.5 |
| Tantalum | Ta | 2,996 ± 50 | 12.4 | 19 |
| Osmium | Os | 2,700 ± 200 | 9.5 | 57 |
| Ruthenium | Ru | 2,500 ± 100 | 7.6 | 42 |
| Rhenium | Re | 3,180 ± 20 | 19.3 | 47 |
| Hard Metal |  | 3,500 |  | 46–63 |
| Ceramic | BN | 3,000 |  | 5–10 |
| Tungsten-Rhenium | W—Re | 3,300 |  |  |

When the present inventor put the above materials to the test, Tungsten, Molybdenum, Hard Metal and Tungsten-Rhenium having a high melting point and a comparatively high Young's Modulus were found to be effective.

In the above experimental example, when the base end of needle 1 is heated to near the melting point (1,400°–1,530° C.), a method for heating by flame, a method based on high frequency induction heating, a method for conducting and heating the needle 1 and the tool 4 (in this conducting and heating method, the electrical resistance of tool 4 should be small), and the like, are effective.

The experimental examples of the present invention will be illustrated in detail as follows:

EXAMPLE 1

Figure 6:
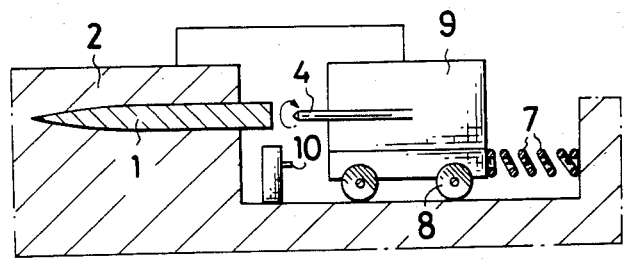
FIG. 6 is a simple diagram of apparatus for performing the method of this invention.

As shown in FIG. 6, the needle 1 is made of 0.6 mm diameter SUS 304 stainless steel and is maintained by the holder 2, while a tip of tool stand 9 having a roller 8 is projected and is provided with the tungsten round linear tool 4 of 0.33 mm diameter and pressed by the pressing spring 7 at 150–200 g pressure. When a voltage of 0.7 V is connected with the needle 1 and the tool 4, an electrical current flows, and the base end of needle 1 is heated to 1200°–1300° C. Tool 4 enters the base end of needle 1 by the operation of press spring 7. When the tool 4 advances to a certain position, a limit switch 10 operates and the voltage becomes zero. When the base end of needle 1 begins to cool gradually, the tool stand 9 is pulled back in the rear and the hole 5 can be formed by pulling out the tool 4 from the base end of the needle 1.

In carrying out the present example, heating temperatures on the base end of needle material 1 were tested by means of three steps, that is, 1,000°–1,100° C. (Voltage 0.55 V), 1,200°–1,300° C. (Voltage 0.7 V) and 1,400°–1,450° C. (Voltage 0.9 V), and the life of tool 4 is longer and the shape of the hole 5 of needle 1 is favorable in the case of 1,200°–1,300° C. temperatures.

EXAMPLE 2

When the conditions are the same as in Example 1 except that the voltage after the operation of limit switch 10 is changed from zero to 0.4 V, the life of tool 4 is longer than in the case of Example 1.

EXAMPLE 3

When the conditions are the same as in Example 1 and the tool 4 has entered the base end of needle 1 while the tool 4 installed on the tool stand 9 is rotated at 500 r.p.m., the life of tool 4 is longer than in the case of Example 1 and shortens the perforating time remarkably.

EXAMPLE 4

Figure 7:
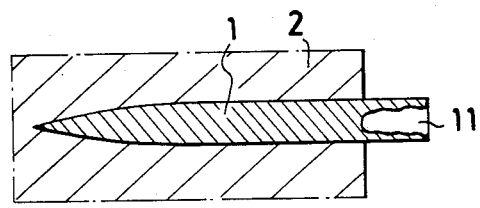
FIG. 7–FIG. 8 are cross-sectional diagrams of other examples.
Figure 8:
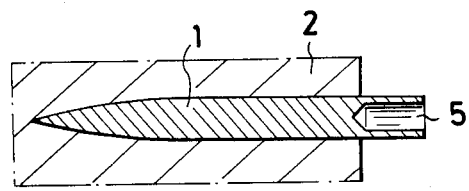

A laser light is used on the base end of needle 1. A preparatory hole 11 of 0.25 mm diameter and 1.6 mm depth as shown in FIG. 7 is bored, and when the conditions are the same as Example 3 a hole forming process is performed with 0.65 V voltage and 1,200°–1,300° C. temperature of the base end of needle 1, the tool 4 can be pressed in the preparatory hole 11 with very small power and the base end of needle 1 is not deformed. The resulting hole 5 can be obtained as nearly a true circle as shown in FIG. 8, and further more the life of tool 4 can be lengthened more than in the above-mentioned examples.

EXAMPLE 5

Figure 9:
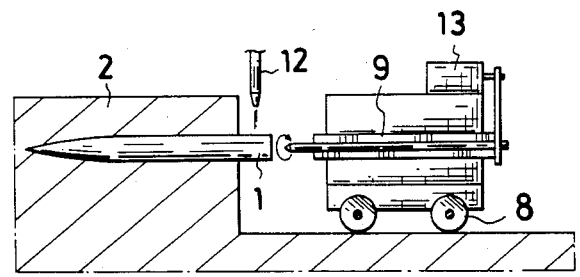
FIG. 9 is a diagram of other apparatus.

A needle 1 made of 0.6 mm diameter SUS 304 stainless steel is maintained by the holder 2 as shown in FIG. 9. A preparatory hole 11 of 0.25 mm diameter and 1.6 mm depth is bored in the base end of needle 1. A tungsten wire of 0.33 mm diameter is used for the tool 4, and the tungsten wire rotates at 500 r.p.m. The base end of needle 1 is heated to 1,200°–1,300° C. by means of burner 12, and the tool stand 9 chucked with tool 4 advances at a speed of 3 mm/sec. by driving the motor 13. The tool 4 simply enters the preparatory hole 11 of needle 1, and a hole 5 of a nearly true circle can be formed in the needle 1. The life of tool 4 can be lengthened remarkably.

EXAMPLE 6

This condition is quite identical as in Example 5, but the formation of hole 5 is performed at the same time that an ultra sonic vibration is applied to the tool 4 and without rotation of the tool 4. The formation of hole 5 is more effective than in the case when the tool 4 is not moved, however as compared with the case when the tool 4 is rotated, the present Example is observed to be inferior in the shape of the hole 5 and the life etc. of tool 4.

EXAMPLE 7

Figure 12:
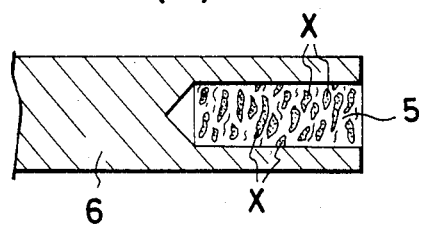
FIG. 12 (*a*), (*b*) are diagrams of another example of a suture needle.
Figure 12:
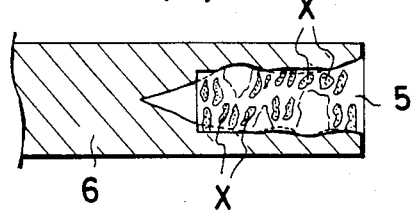

The needle 1 is of 0.8 mm SUS 304 stainless steel and a hole of 0.47 mm diameter is completed in the needle material with drill and laser light by means of an experimental apparatus as shown in FIG. 9. The tool 4, which is composed of 0.47 mm diameter tungsten wire, is rotated at 500 r.p.m. as the needle material 1 is heated to 1,400°–1,500° C. by the burner 12. The tool 4 is inserted into the hole in the needle material 1 with speed of 3 mm/sec. When the base end of needle 1 containing the hole is divided into two parts lengthwise and the inner wall surfaces are observed through a microscope, the inner wall surfaces according to the drill hole and the laser hole are nearly a mirror surface, while a spiral-shaped uneven X produced by a stream of material at high temperature has been formed at the inner wall surfaces as shown in FIG. 12a (drill hole) and FIG. 12b (laser hole), as those in FIGS. 3, 4, and 5. A thread is inserted into the hole 5 turning out this state and the hole 5 is subjected to a caulking processing. Subsequently, as a result of measuring the extracting power of the thread, a result indicating large extracting power is obtained, namely an average increase of 45% in the drill hole and an average increase of 90% in the laser hole by processing the inner wall surface, as compared with a hole having no processing in the inner wall surface.

When the present method is carried out as mentioned above, and the principle under which an uneven X is formed automatically in the inner wall surface of the hole 5 of needle 1 (suture needle 6) is considered, when the perforating tool 4 is inserted into the needle 1 heated to near the melting point as the perforating tool 4 rotates, the tool 4 comes in contact with the substance so that the needle 1 turns into the states of exactly hard paste and proceeds as this paste-like material is rubbed, and in the inner wall surface of the hole 5 formed by the tool 4, an uneven X remains in that condition together with dropping the temperature of needle material 1.

Figure 10:
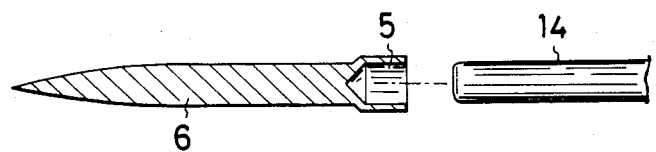
FIG. 10–FIG. 11 are cross-sectional diagrams of another suture needle and showing the installation of the thread.
Figure 11:
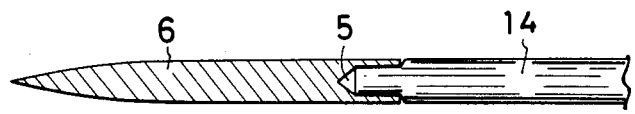

Since the method in accordance with the present invention is a method that involves a perforation performed by making forcibly a heat resisting perforating tool enter the base end while the base end of the needle material is heated to near the melting point of the needle material, the method can be performed simply and reliably. A hole with good capability for attaching thread is provided, as opposed to that of the prior art wherein the operation of the prior art process is complex and the work efficiency is poor. In the drill cutting method, pipe welding processing method, electrical discharge perforation method and laser, electron beam processing method and the like in the prior art, if the prior art method is utilized as the secondary processing method of perforation by rotating the tool 4, the method can be considered as a method for forming the inner wall surface of the hole, and the tool employed can be a wire of heat resisting material, and the method is inexpensive and can remarkably lengthen the life of the hole. Accordingly, the method of the present invention is suitable to the processing of stainless needles (especially austenite system), the processing of which was previously considered to be relatively difficult. In the method of the present invention, when the austenite system stainless steel or the precipitation hardening type stainless steel is used without conducting a quench hardening processing of the whole needle at the end of the process, since the needle material is heated to near the melting point at the time of processing, the base end softens (for example the whole needle makes a hole portion Hr 200 against Hr 500), and at the time of caulking the caulking power is small and the base end is easy to fit with the thread and the thread extracting power becomes large. Heretofore the deficiency resulted from the inner part, but this now has a character in which the deficiency is not produced. Furthermore, when the present invention is carried out, as shown in FIG. 10, a suture needle in which an outer diameter of the base end of the needle 1 around this hole 5 is larger than other portions, the suture needle 6 constituted in this manner is utilized positively with the state as it is, after the thread 14 is inserted in the hole 5, by means of caulking this larger diameter portion, as shown in FIG. 11. A special suture needle such that an outer diameter of the base end of the suture needle becomes nearly equal to the outer diameter of thread 14 can be manufactured automatically by omitting the process in the midst of carrying out the present method. Moreover, in the case of rotation of the tool when the present invention is carried out, the unevenness and the oxidized adhesive in accordance with a compulsory stream of material at high temperature in the inner surface of the hole can be formed, and therefore the installing capability of the thread to the hole can be raised remarkably. The formation of the inner wall surface can be utilized independently for the secondary processing of the usual method, and the present method has various characteristics as mentioned above.

I claim:

1. A method of forming an eyeless suture needle having a tapered end, an intermediate portion, and a base end, the base end having a hole, said method comprising: providing a needle material having oxidation resistance; providing a heat resistant pressing tool having a melting point higher than that of the needle; positioning the needle in a holder with the base end of the needle extending beyond the holder; providing a tubular restraining tool having an inner diameter larger than the outer diameter of the needle to surround the base end of the needle; heating the base end of the needle to a temperature near its melting point; pressing the heat resisting perforating tool into the base end of the needle material while the base end of the needle material is near its melting point to form a hole and an enlarged circumferential outer surface defined by the interior of said tubular restraining tool; and cutting off part of the enlarged circumferential surface to provide a needle of uniform outer diameter at its base end and intermediate portion.

2. The method for an eyeless suture needle as claimed in claim 1, including the step of boring a preliminary hole in said needle before the base end of the needle material is heated to near its melting point and before the pressing step.

3. The method of forming an eyeless suture needle as claimed in claim 1 or 2, including the step of rotating the perforating tool as it is pressed into the base end of the heated needle material.

4. The method for forming an eyeless suture needle as claimed in claim 2, wherein the boring step for the preliminary hole is performed by laser processing.

5. The method for forming an eyeless suture needle as claimed in claim 2, including the step of contacting the inner wall surface of the preliminary hole with a rotating perforating tool to impart unevenness to the inner surface of the hole based on the flow of material formed in the direction of the wall surface by rotating and contacting the heat resisting perforating tool to the inner wall surface of the hole while the preliminary hole is heated to near the melting point, and after the preliminary hole is bored in the base end of the needle material.

6. The method for forming an eyeless suture needle as claimed in claims 1, 2 or 5, wherein a round rod made of a material selected from the group consisting of tungsten, molybdenum, hard metal, and tungsten rhenium is used for the heat resistant perforating tool.

7. The method of forming an eyeless suture needle as claimed in claims 1, 2 or 5, wherein the heating step includes heating the base end of the needle material to 1,000°–1,600° C. by conducting electricity to the needle material and the perforating tool.

8. The method for forming an eyeless suture needle as claimed in claims 1, 2 or 5, wherein the heating step includes heating the base end of the needle material to 1,000°–1,600° C. by means of a flame.

9. The method for forming an eyeless suture needle as claimed in claim 1 or 2, including the step of vibrating the perforating tool as it is pressed into the base of the needle material.

10. The method for forming an eyeless suture needle as claimed in claim 2, wherein the boring step for the preliminary hole is performed by electron beam processing.

* * * * *